(12) United States Patent
Aranciva (10) Patent No.: US 9,033,891 B2
(45) Date of Patent: May 19, 2015

(54) MULTICHAMBER SPHYGMOMANOMETER WITH CHAMBER SELECTOR

(76) Inventor: Ricardo Rodriguez Aranciva, San Luis (AR)

( * ) Notice: Subject to any disclaimer, the term of this patent is extended or adjusted under 35 U.S.C. 154(b) by 1542 days.

(21) Appl. No.: 12/465,499

(22) Filed: May 13, 2009

(65) Prior Publication Data

US 2009/0287100 A1      Nov. 19, 2009

(30) Foreign Application Priority Data

May 14, 2008  (AR) ................................ P080102034
May 12, 2009  (AR) ................................ P090101710

(51) Int. Cl.
  *A61B 5/02*       (2006.01)
  *A61B 5/022*      (2006.01)
  *A61B 5/0235*     (2006.01)

(52) U.S. Cl.
  CPC ........... *A61B 5/02233* (2013.01); *A61B 5/0235* (2013.01)

(58) Field of Classification Search
  USPC ..................... 137/625.48; 251/325
  See application file for complete search history.

(56) References Cited

U.S. PATENT DOCUMENTS

| | | | | |
|---|---|---|---|---|
| 4,210,154 A  * |  7/1980 | Klein | ............................ | 600/498 |
| 4,572,205 A  * |  2/1986 | Sjonell | .......................... | 600/499 |
| 4,920,971 A  * |  5/1990 | Blessinger | .................... | 600/492 |
| 5,464,019 A  * | 11/1995 | Anderson et al. | ............. | 600/490 |
| 5,626,142 A  * |  5/1997 | Marks | ............................ | 600/499 |
| 2007/0073174 A1 * |  3/2007 | Aranciva | ....................... | 600/499 |

* cited by examiner

*Primary Examiner* — Navin Natnithithadha
*Assistant Examiner* — Michael R Bloch
(74) *Attorney, Agent, or Firm* — Ladas & Parry LLP (57) ABSTRACT

A multichamber sphygmomanometer is provided with a set of inflatable chambers (2) that may be selectively used and connected to the air pressure pump (20) by means of a chamber selector device (4). In an embodiment, the selector device (4) operates through assigned manual connections (5) and selective connections (6). In another embodiment, the selector device (4) has a selection controller (4*c*) which valve shutter (4*b*) operates between an inlet path (7) corresponding to the air pressure pump (20) and the outlet paths (6) corresponding to the inflatable chambers (2), including the possibility to use a positional identification system (10) which allows selecting (8) the most appropriate chamber (2) for each case.

7 Claims, 9 Drawing Sheets

MULTICHAMBER SPHYGMOMANOMETER WITH CHAMBER SELECTOR

FIELD OF THE INVENTION

The present invention refers to the field of medicine, veterinary and the instruments to measure blood pressure.

More particularly, it consists of a multichamber sphygmomanometer with chamber selector, able to be adapted to the different sizes of the limbs to which it is applied, by means of chambers that may be selected through a selector device.

STATE OF THE ART

Up to date, different types of sphygmomanometers which use two or more inflatable chambers are known.

For example, the patent document U.S. Pat. No. 4,572,205 discloses some chambers where the air flow is supplied through a single and main tube passing through secondary branches towards the chambers. Enabling the different chambers depends on the position that a hook or claw is placed.

The patent document U.S. Pat. No. 4,210,154 displays a simple of a device having an acoustic chamber and two chambers of different sizes or length along the armlet to be used around limbs or parts of the body with different sizes. These chambers work with a switch to select the chamber to use, thus, it has alternative outlets and only one chamber can be used at a time.

The patent document U.S. Pat. No. 5,626,142 discloses a multiple system that, on an ordinary structure, indicator and tire pump, has several armlets of different sizes available, each of them may be enabled by means of a corresponding pneumatic switch. It is a very large, not handy and not practical system.

Patent documents GB 1400957 and U.S. Pat. No. 3,906,937 disclose a compartmentation chamber, wherein all the compartments communicate with each other, so that through a common path, all the compartments get inflated at the same time.

Other devices are known, such as, for instance, those disclosed by the following patent documents:
  The patent documents JP2004254717 and U.S. Pat. No. 5,511,551 wherein several chambers that are inflated together to obtain uniform pressure can be observed.
  The patent documents U.S. Pat. Nos. 3,118,440 and 4,667,672 wherein annular chambers communicated between each other can be observed.
  The patent documents U.S. Pat. Nos. 3,348,534 and 3,581,734 wherein inflatable chambers with comparison electronic circuits can be observed.
  The patent document U.S. Pat. No. 3,699,945 wherein the use of signs that identify different adjustment positions of the armlet are observed.
  The patent document U.S. Pat. No. 3,752,147 wherein a set of overlapping inflatable chambers are shown.
  The patent document U.S. Pat. No. 5,464,019 wherein an automatic control system with two paths for different chamber can be observed.
  The patent documents US 2001/0016692 and US 2003/0055347 show some overlapping chambers and communicated between each other.
  The patent document US 2004/0181254 shows a device with a major and a minor chamber, overlapped.

Another device known is that disclosed by applications AR-P 040103230, AR-P050101482, U.S. Ser. No. 11/222,617 and BR-PI 0503972-0 by the same inventor of the present invention. The sphygmomanometers disclosed therein, are of the multichamber type but based on rotary action valve selector devices which are very large, troublesome to handle and expensive.

ADVANTAGES AND PURPOSES

An object of the present invention is to simplify the operation of the sphygmomanometer, especially with reference to the manner of selection of the inflatable chambers to use.

Another objective is to provide a sphygmomanometer wherein inflatable chambers combine with a valve selector device much easier to handle than the rotary action devices.

An advantage of the present sphygmomanometer is that it is appropriate to measure the blood pressure to persons with different size limbs (adults, teenagers, children, newly born, with normal or abnormal height, obese, malnourished, eutrophic, etc.). It may even obtain a perfect adaptation in the case of obese patients with cone-shaped arms. Consequently, it may be adapted to people with different physical condition, age and nutritional condition to obtain an accurate measurement of blood pressure according to each type of patient in particular. This is possible because independent inflatable chambers are available for different limb sizes, so, the most appropriate chamber or set of chambers may be selected for each case.

Another advantage is that it may work with different amounts of inflatable chambers allowing the increase or lowering of its selective capacity according to each need.

Another advantage is that, in any of its embodiments, different size chambers can be enabled, thus ensuring the possibility to select that chamber which size allows surrounding the entire brachial perimeter of the patient's limb. In this manner, the inconvenience of conventional sphygmomanometers that usually cover said brachial perimeter partially is eliminated.

Other important advantages derived from a rectilinear valve selector device are the following:
  It may be operated more easily tan the rotary action devices.
  The device is not so large and may be applied to the armlet without too much projection.
  It facilitates the assembly of the device in the armlet.
  With the manual connection system as well as with the sliding mechanism of the valve selector device, the own failures of the rotary system are avoided.
  It allows that the enabling of chambers may be done in two different modes: alternative selection of chambers or integrating and disintegrating chambers, either.
  It lowers the costs of the selector device.
  It allows incorporating the selector device to the operative body or support of the sphygmomanometer.

A further advantage is that, having identifying means of the chambers arranged on the armlet and the connection means, the operation is extremely simple. In fact, the armlet is simply placed surrounding the patient's limb until the end applied matches an identifier means, and afterwards, the position corresponding to said identifying means is selected in the valve selector device. In this manner, the corresponding inflatable chamber is enabled.

A further advantage is that the set of chambers as well as their connection means may be changed as necessary.

Another advantage is that, having several fixation means which substantially cover the armlet walls, the latter may be used totally or partially, according to the size of the patient's limb and the chamber to be used.

Another advantage is that the capacity of selecting different chambers which measures will be standardized will largely facilitate the performance of statistics.

A further advantage is that it refers to a sphygmomanometer which large capacity for different uses does not have a negative incidence in its size, therefore, it can be easily carried into small cases or containers, into suitcases, briefcases, etc.

BRIEF DESCRIPTION OF THE DRAWINGS

For better clarity and understanding of the object of the invention, it is illustrated with several figures wherein it has been represented in one of its preferred embodiments, only as an illustration, but not limiting:

FIG. 9 comprises drawings A and B, where:

Drawing A, an upper view, exploded, of the valve selector device in another embodiment; the selection controller and the positional identification system may be appreciated; and
Drawing B, a side elevated view, of the same valve selector device where the inlet connection is observe on the upper portion.

In the different figures, the same reference numbers and/or letters indicate equal or corresponding parts.

List of the main references:

| | |
|---|---|
| (1) | Armlet. |
| (1a) | Passage opening. |
| (1b) | Armlet tightening means (1). |
| (2) | Set of inflatable chambers. |
| (2a) | First inflatable chamber. |
| (2b) | Second inflatable chamber. |
| (2c) | Third inflatable chamber. |
| (3) | Inner pneumatic tubes. |
| (3a) | First inner pneumatic tube. |
| (3b) | Second inner pneumatic tube. |
| (3c) | Third inner pneumatic tube. |
| (4) | Selector device [of manual connection or rectilinear valve]. |
| (4a) | Distribution passage [of the valve selector device (4)]. |
| (4b) | Valve shutter [of the valve selector device (4)]. |
| (4c) | Selection controller [of the valve selector device (4)]. |
| (5) | Pneumatic outlet connections [for the inner pneumatic tubes (3)]. |
| (5a) | First connection of pneumatic outlet. |
| (5b) | Second connection of pneumatic outlet. |
| (5c) | Third connection of pneumatic outlet. |
| (5d) | Fourth connection of pneumatic outlet [if there is a fourth inflatable chamber]. |
| (6) | Pneumatic outlet paths/outlet selective connection. |
| (6a) | First outlet path/first selective connection. |
| (6b) | Second outlet path/second selective connection. |
| (6c) | Third outlet path/third selective connection. |
| (6d) | Fourth outlet path/fourth selective connection [if there is a fourth inflatable chamber]. |
| (7) | Inlet path. |
| (8) | Connection of pneumatic inlet. |
| (9) | Outer pneumatic tube. |

-continued

List of the main references:

| | |
|---|---|
| (10) | Positional identification system or identifying signs of inflatable chambers (2). |
| (10a) | First positional identifier. |
| (10b) | Second positional identifier. |
| (10c) | Third positional identifier. |
| (10d) | Fourth positional identifier [if there is a fourth inflatable chamber]. |
| (14a) | Controlling arm. |
| (14b) | Controlling socket. |
| (14c) | Controlling guide. |
| (14d) | Controlling track. |
| (15) | Valve means [o-ring]. |
| (20) | Air pressure pump or chamber air pressure pump (2). |
| (20a) | Operative support or sphygmomanometer body. |
| (20b) | Valve means. |
| (20c) | Grip. |
| (21) | Manometer to indicate the pressure. |

DESCRIPTION

In general terms, the present invention refers to a multi-chamber sphygmomanometer with chamber selector provided with a set of inflatable chambers (2) that may be selectively used and connected to the air pressure pump (20) by means of a chamber selector device (4). In an embodiment, the selector device (4) Works through assigned manual connections (5) and selective connections (6). In another embodiment, the selector device (4) has a selection controller (4c) which valve shutter (4b) works between an inlet path (7) corresponding to the air pressure pump (20) and the outlet paths (6) corresponding to the inflatable chambers (2), including the possibility to use a positional identification system (10) that allows selecting (8) the most appropriate chamber (2) for each case.

DETAILED DESCRIPTION

More particularly, the present multichamber sphygmomanometer is intended to measure blood pressure. For that purpose, on the one hand, it has an armlet (1) able to surround a limb to measure its blood pressure. On the other hand, the sphygmomanometer also has an air pressure pump (20), a manometer (21), a releasing valve means (20b) and an outer pneumatic tube (9) that connects the inflatable chambers (2) with the air pressure pump (20) and the manometer (21). [The latter may be from different types, for example, mercurial, aneroid, digital, electronic, automatic, semiautomatic, with or without remote control, etc.]

The walls of the armlet (1) form a housing into which a set of inflatable chambers (2) is arranged. This set (2) may be integrated by two or more inflatable chambers (2a) (2b) (2c).

Figure 5:
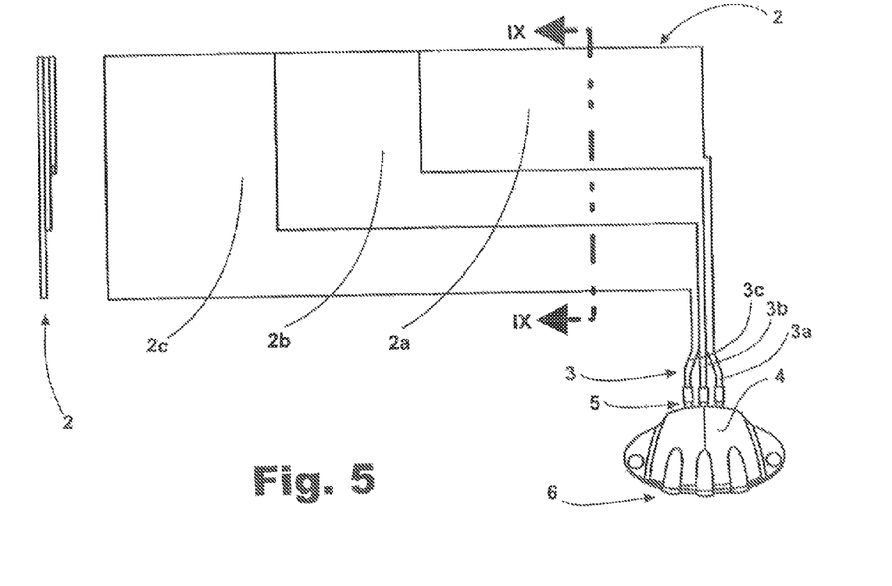
FIG. 5 comprises a side view of a set of rectangular chambers that, for example, may be defined by compartmentation or by chamber joint, either. On the left, a transverse view can be observed appearing as IX-IX on the side view.
Figure 6:
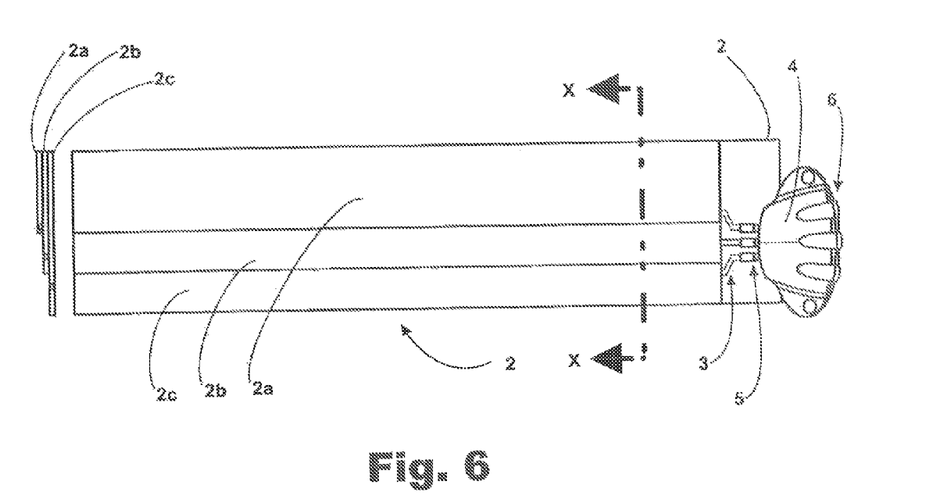
FIG. 6 comprises a side view of a set of rectangular longitudinal overlapping chambers. On the left, a transverse view indicated as X-X can be seen on the side view.

These inflatable chambers (2) have different capacity, and they may have different extension, different height, different extension and height, may be several chambers (2a)(2b)(2c) formed from common walls or partings that form compartments of different capacity into the housing, may be several overlapped chambers (2a)(2b)(2c), one chamber adjacent to the other, etc.

Regardless the variant used each chamber (2) always connects to a respective connection of pneumatic outlet (5). This connection may be direct or either through a respective inner individual pneumatic tube (3).

In this last case, each individual inner pneumatic tube (3a) (3b) (3c) is connected to a respective pneumatic outlet connection (5a) (5b) (5c).

These pneumatic outlet connections (5) correspond to a valve selector device (4) which also has a pneumatic inlet connection (8) connectable to the outer pneumatic tube (9) and, through the latter, to the air pressure pump (20).

Figure 1:
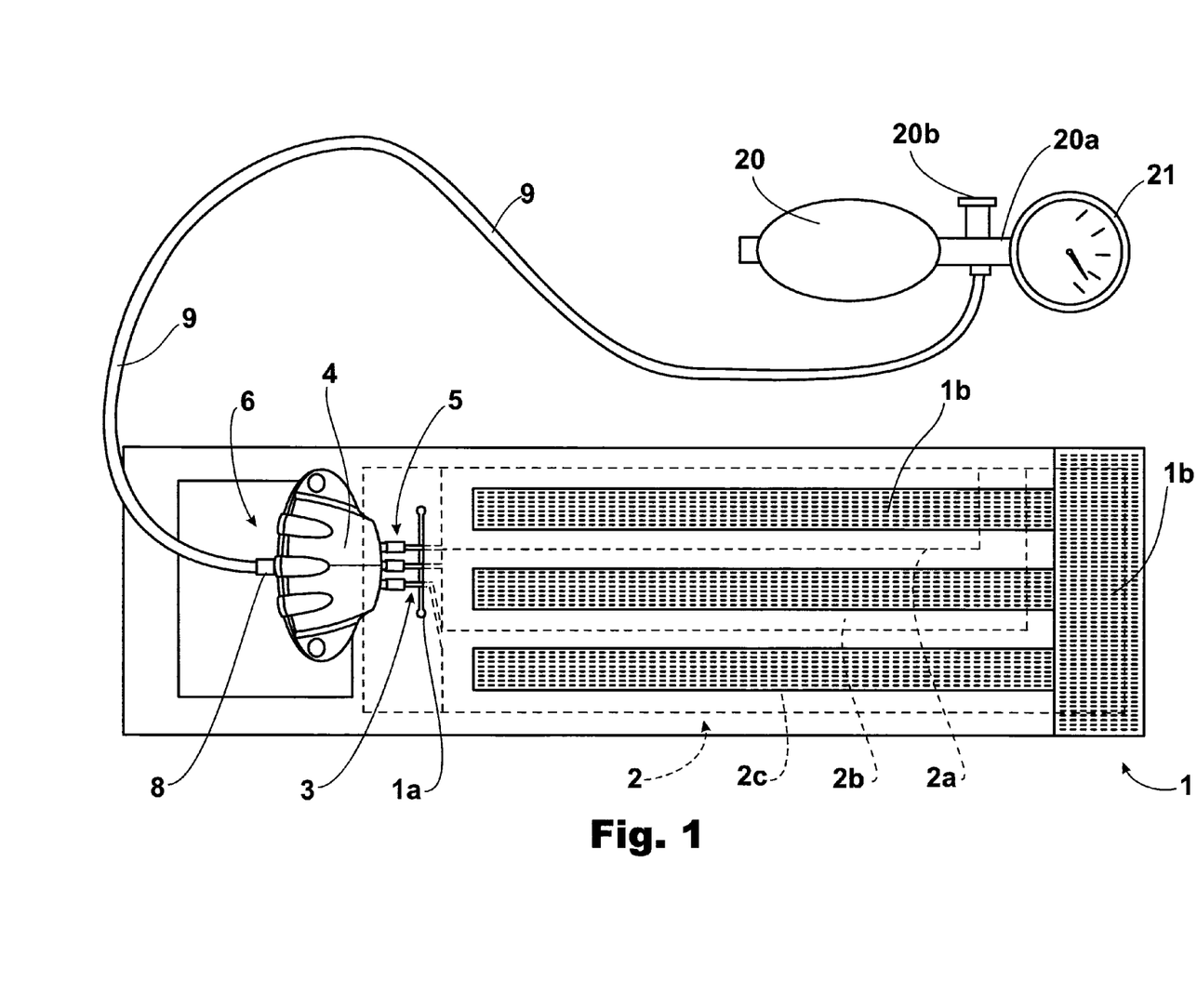
FIG. 1 is a side elevated view of the present sphygmomanometer where it can be appreciated the arrangement of the manual connection selector device and its relation with the chamber, on the one hand, and with the air pressure pump, on the other.
Figure 4:
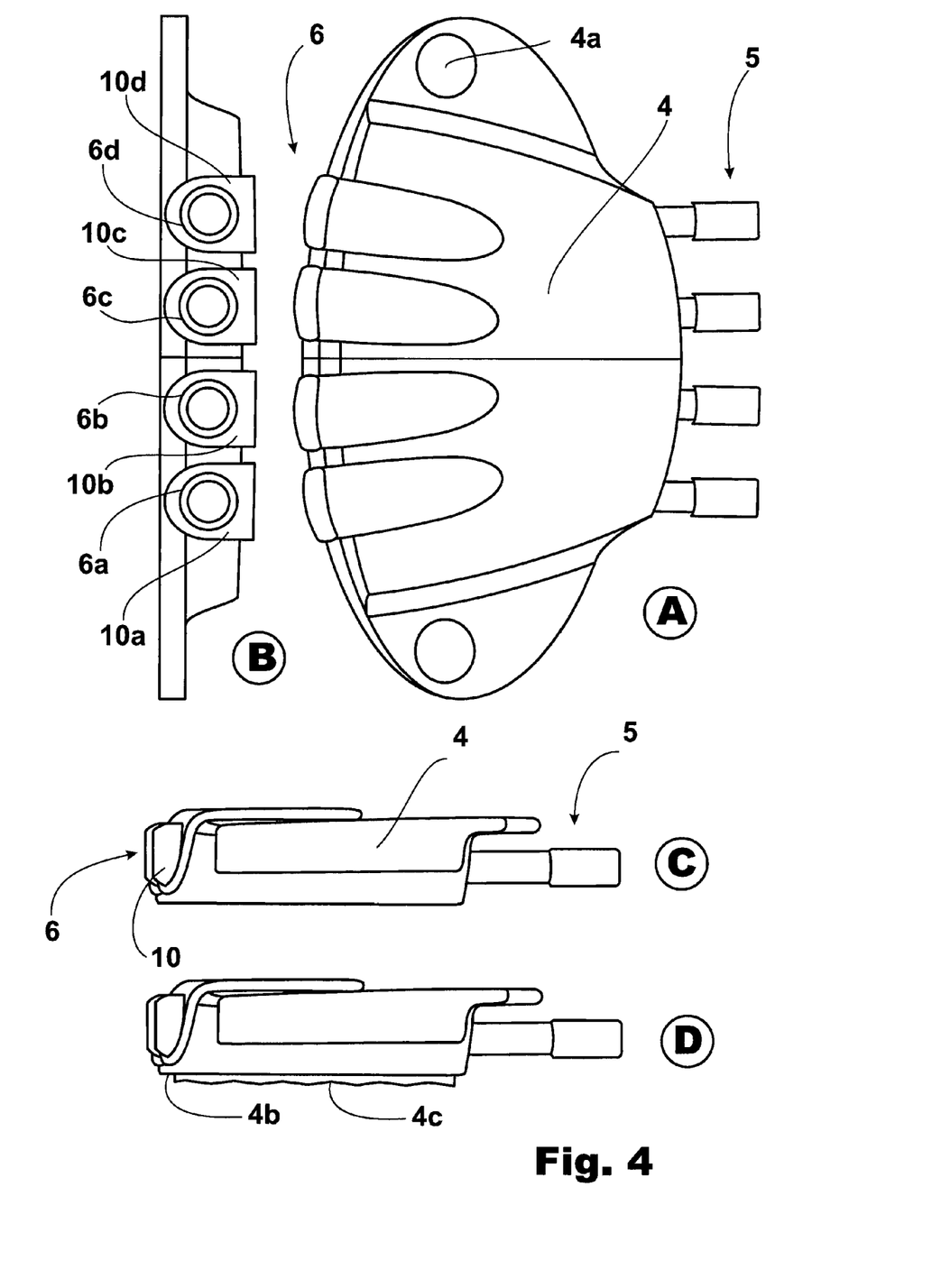
FIG. 4 comprises drawings A, B, C and D, where:
Drawing A, an upper elevated view of the connection means or manual selector device that provides the assigned connections and the selective connections to relate the set of chambers with the air pressure pump and the pressure indicator; it may present, on this face, indicators of color, numerical, etc. of paths to select in a visual and/or tact manner presented in over relief or bas-relief matching the designations of the chambers on the armlet scales,
Drawing B, a front elevated view of the manual selector device,
Drawing C, a side elevated view of the manual selector device; and
Drawing D, a side elevated view of the manual selector device in an embodiment which comprises a self-adhesive wall of the Velcro type.

In the case of the manual connection selector device, each chamber (2) connects with a respective assigned connection (5). This connection may be direct or either through a respective inner individual pneumatic tube (3). In this latter case, each inner individual pneumatic tube (3) connects to a respective assigned connection (5).

These assigned connections (5) are arranged in a pneumatic connection structure (4) that, able to have different arrangements, includes some selective connections (6). For each assigned connection (5a) (5b) (5c) (5d), there is a respective selective connection (6a) (6b) (6c) (6d) with which it communicates.

Together with that, the assigned connections (5) as well as the selective connections (6) may project with different orientations from the structure (4), even with different orientations in relation to each other.

On the other hand, the above mentioned connection structure (4) may form the tubes on which ends the assigned connections (5) and selective connections (6) are placed, or said tubes may be incorporated to it.

In addition, the assigned connections (5) and the inner pneumatic tubes (3), on the one hand, as well as the selective connections (6) and the selector connector (8), on the other hand, may be of the box and pin type, being enough for them to possess the capacity to allow their adequate connection.

The selective connections (6) are available so that in any of them, it may be connected the selector connector (8) that, through the outer pneumatic tube (9), allows the connection with the air pressure pump (20).

Figures 7, 8:
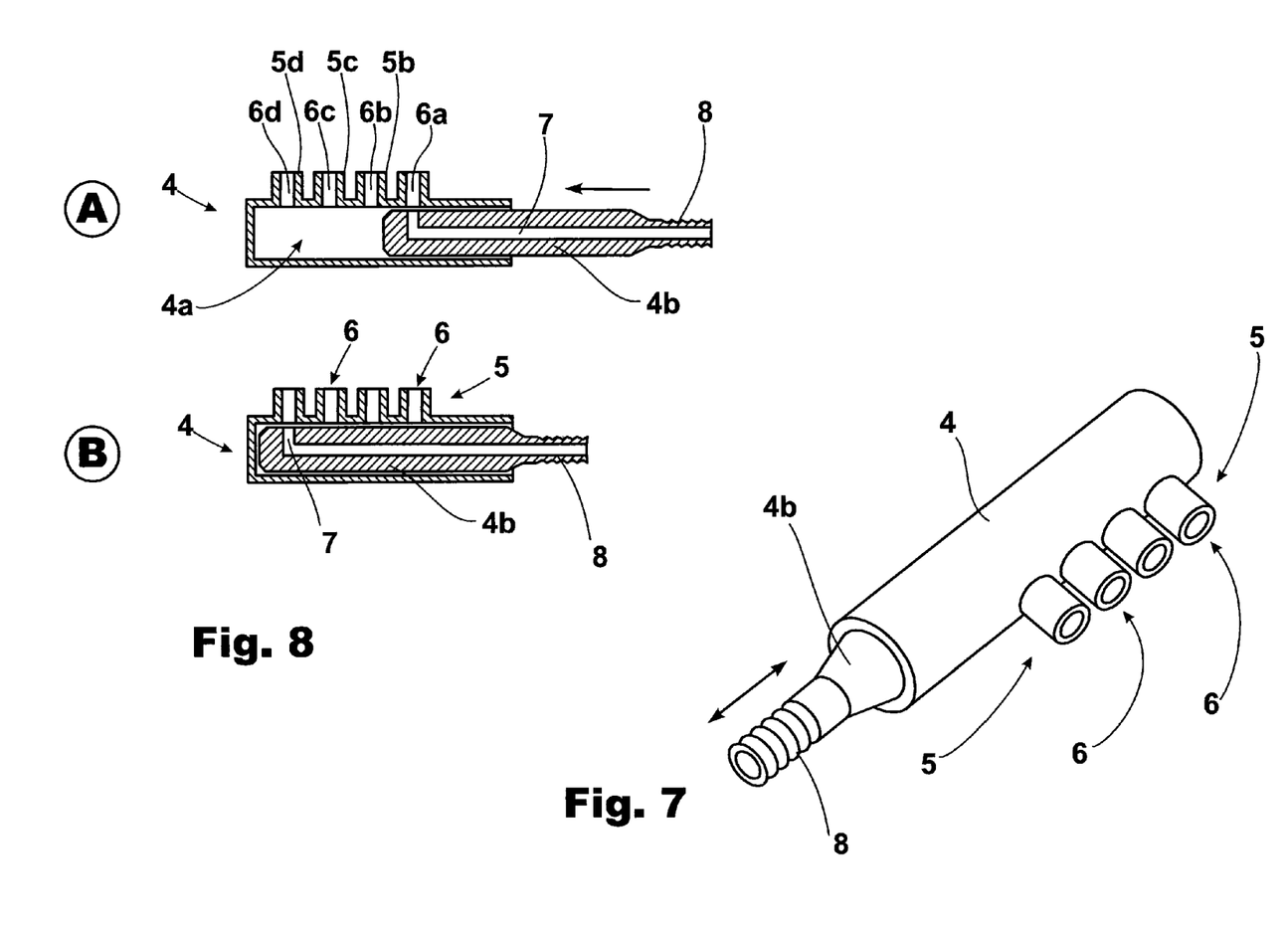
FIG. 7 is a perspective view that shows an embodiment of the valve selector device.
FIG. 8 comprises drawings A and B, where:
Drawing A, a longitudinal section of the valve selector device of FIG. 7, in a position where the first connection of pneumatic outlet is enabled; and
Drawing B, another longitudinal section of the valve selector device of FIG. 7, in another position where the fourth connection of pneumatic outlet is enabled.

In the case of the valve selector device (4), it works as a rectilinear distribution valve. It comprises a main body into which, there is a rectilinear distribution passage (4a). Through this distribution passage (4a) are communicated an inlet path (7) [corresponding to the pneumatic inlet connection (8)] with some pneumatic outlet paths (6) [corresponding to the pneumatic outlet connections (5)].

Figure 12:
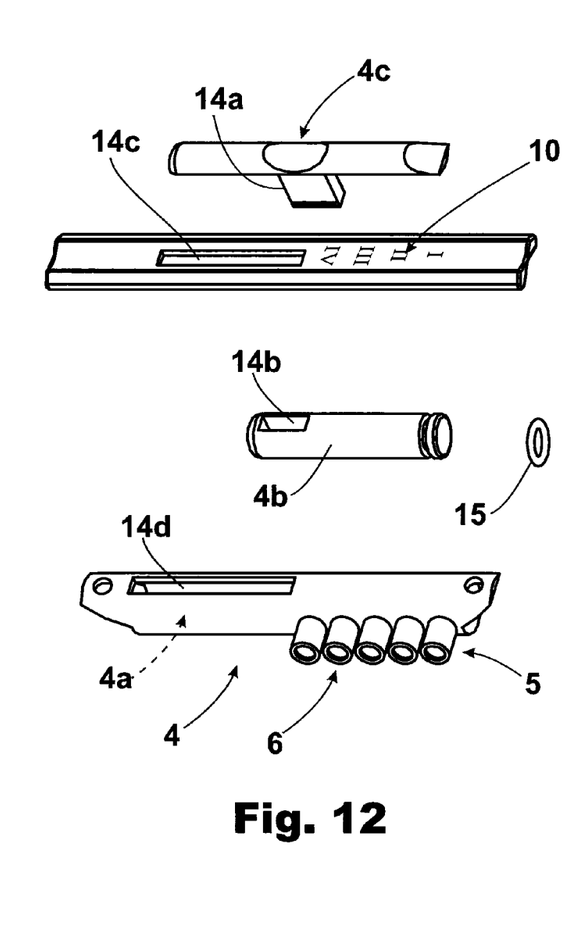
FIG. 12 is a perspective view corresponding to an exploded view of the valve selector device, wherein the different components can be observed.

To control this communication between paths (7)(6), into the distribution passage (4a) works slidingly the valve shutter (4b)—which may have means such as one or more o-rings (15)—operated through a selection controller (4c). In a possible embodiment, the above mentioned selection controller (4c) operates in solidarity with said valve shutter (4b) by means of a controlling arm (14a) and a controlling socket (14b). This controlling arm (14a) passes through a controlling guide (14c) and track (14d). Equally apt are the valve shutters (4b) with one or more valve means (15) that, according to the needs, may serve for alternative communication—selecting the chamber (2)—as well as for the cumulative communication—adding chambers (2)—between the inlet path (7) and each outlet path (6).

Figure 13:
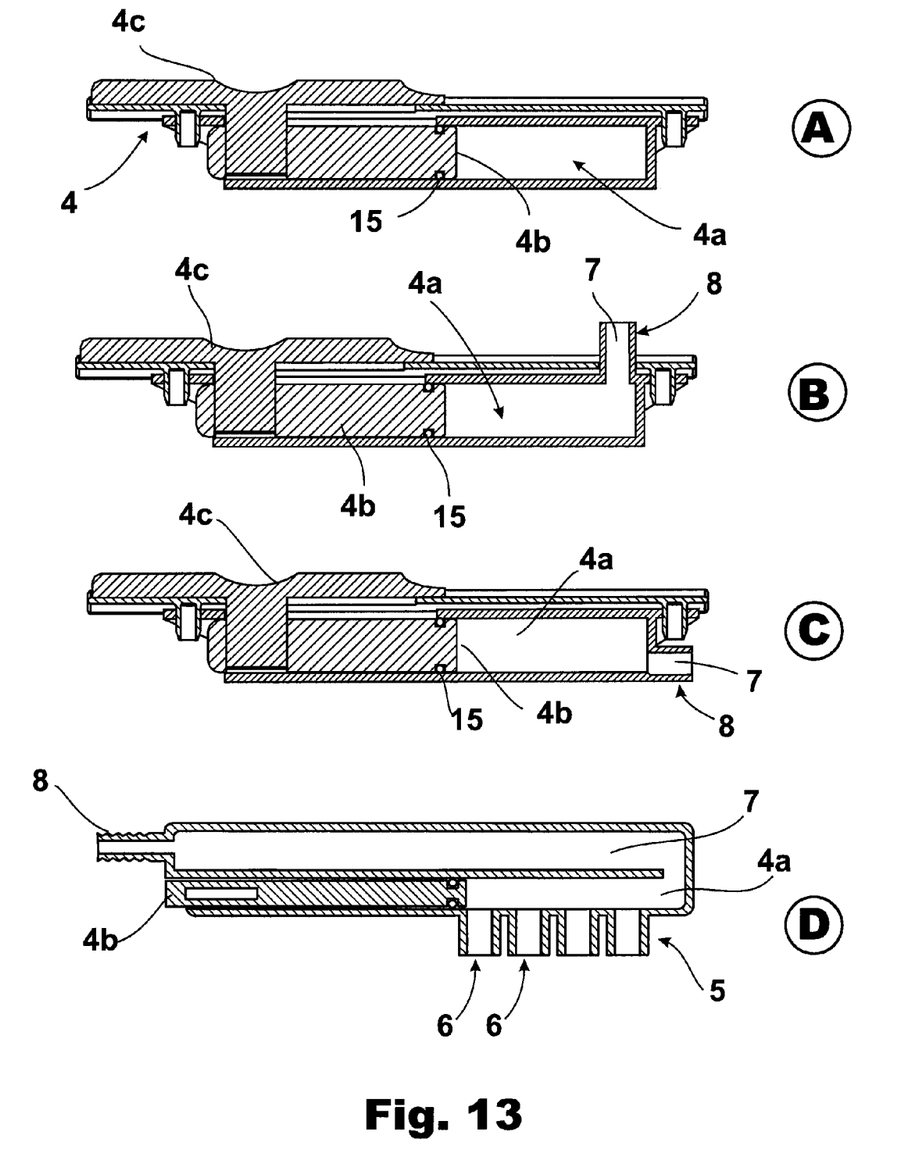
FIG. 13 comprises drawings A, B, C and D, where:
Drawing A, a longitudinal section of a valve selector device with side inlet connection,
Drawing B, a longitudinal section of a valve selector device with upper inlet connection,
Drawing C, a longitudinal section of a valve selector device with front inlet connection; and
Drawing D, an upper exploded view of a valve selector device with posterior inlet connection.

It has been considered that the outlet connections (5) as well as the inlet connection (8) may project with different orientations from the body of the selector device (4), even with different orientations one in relation to the others.

Figure 2:
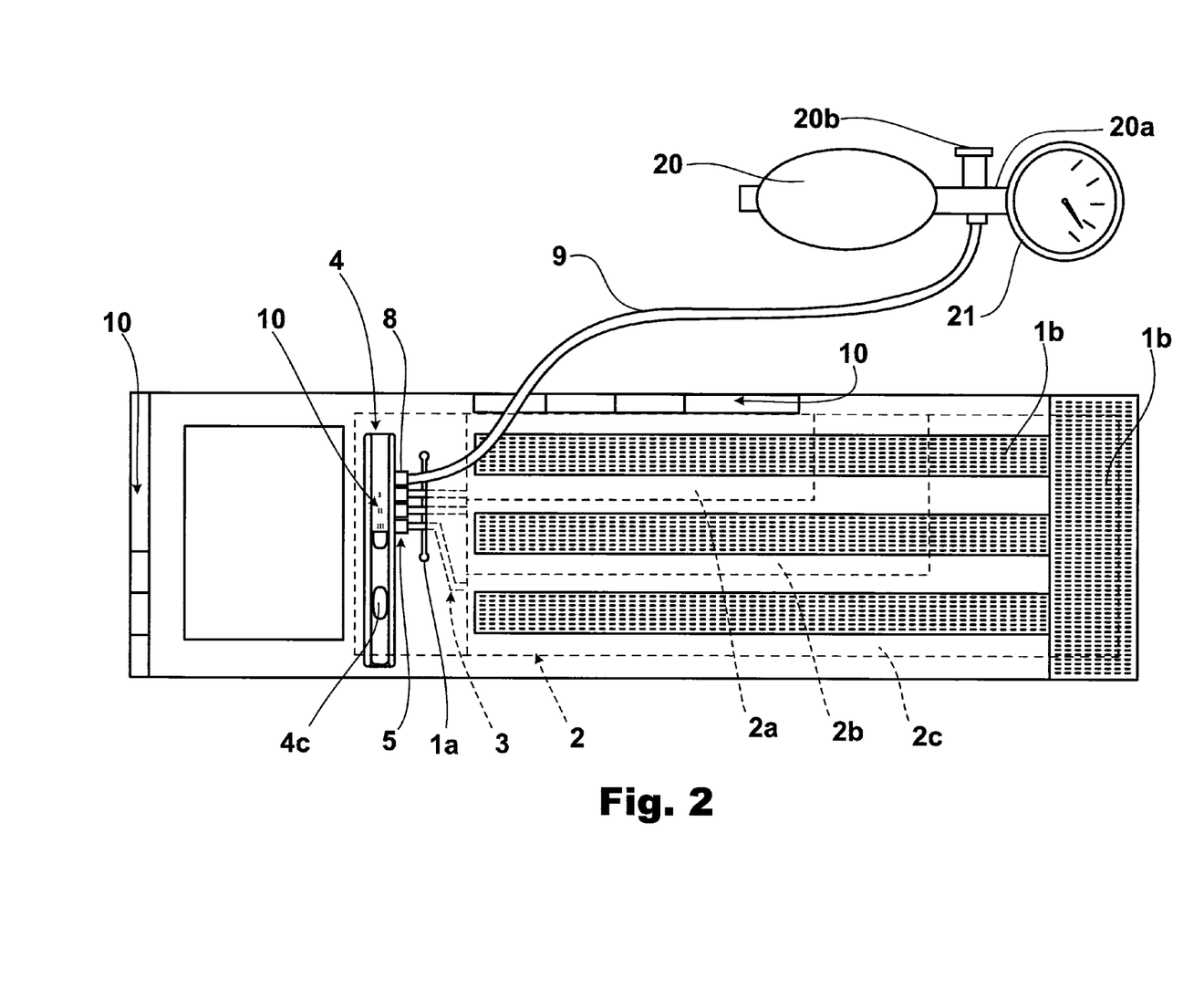
FIG. 2 is a side elevated view of the present sphygmomanometer where it can be appreciated the arrangement of the valve selector device and its relation with the chambers, on the one hand, and with the air pressure pump, on the other. It can also be observed a color indicating scale adjacent to a transversal edge and another color indicating scale adjacent to a longitudinal edge. In addition, it can be appreciated that the inner pneumatic tubes emerge through a passage opening.

In addition, the selector device (4) may be arranged in the armlet (1), close to one or more passage openings (1a) that communicate with the inner housing of said armlet (1) and allows the outlet of the individual pneumatic tubes (3). Thus, the latter (3a) (3b) (3c) may be connected to the respective outlet connections (5a) (5b) (5c).

Figure 10:
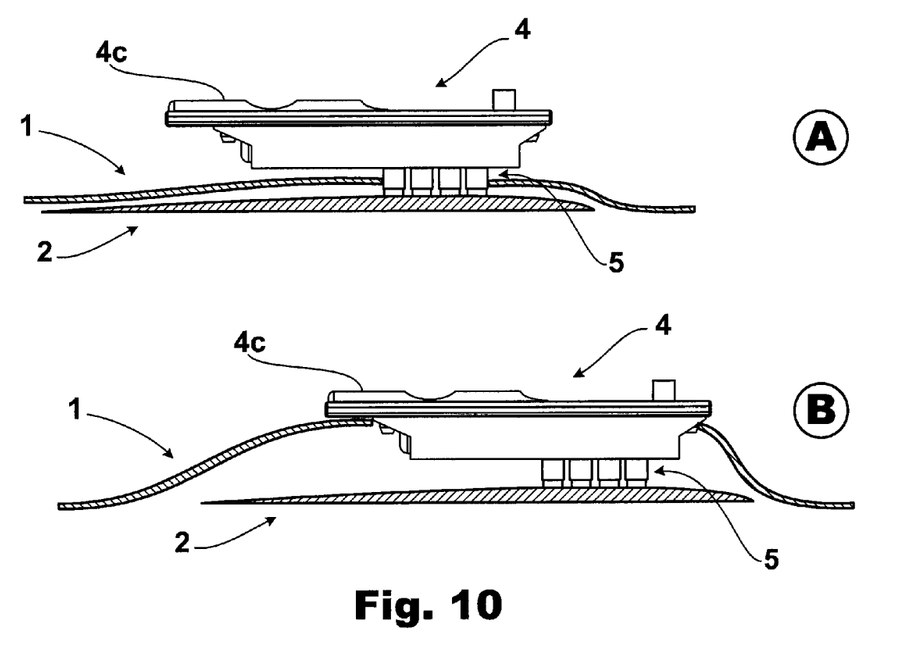
FIG. 10 comprises drawings A and B, where:
Drawing A, a side elevated view of the selector device mounted outside the armlet and connected to the inflatable chambers; and
Drawing B, a side elevated view of the selector device partially mounted into the armlet and connected to the inflatable chambers.

With reference to the location of the selector device (4), it be close to the passage opening (1a) out of the armlet (1) or into it. In this last variant, at least, the selection controller (4c) will be outwardly accessible.

For the relation between the selector device (4) and the armlet (1), it is possible to have different means available, for example, some fixation wings [for rivets, anchorages, sewing, etc.], a dismountable support, a self-adhesive wall of Velcro type [e.g., at the base of the main body], several adhesive and/or fixing means or any other equivalent means [not illustrated].

Figure 9:
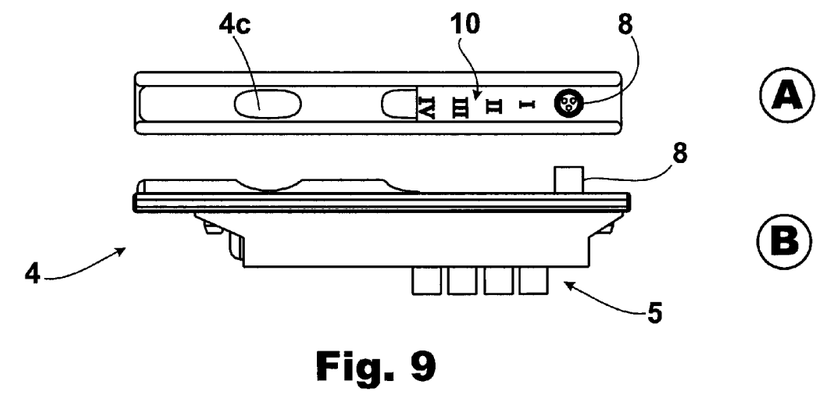
Figure 11:
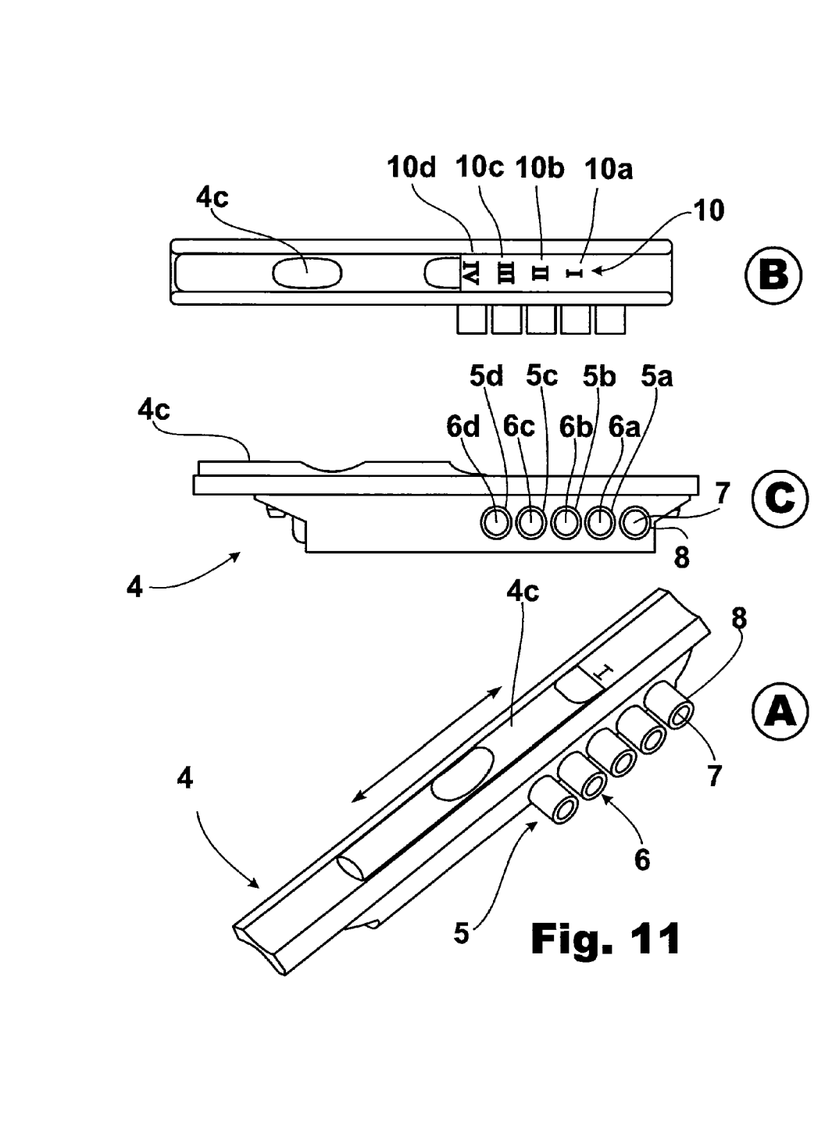
FIG. 11 comprises drawings A, B and C, where:
Drawing A, a perspective view of the valve selector device wherein the positional mobility of the selector controller is indicated,
Drawing B, an upper exploded view of the same valve selector device wherein the positional identification system can be appreciated; and
Drawing C, side elevated view of the same valve selector device where the inlet connection is observed on the side portion adjacent to the outlet connections.

In a preferred embodiment, the sphygmomanometer will have a positional identification system (10) that will allow selecting the chamber with which (2a) (2b) or (2c), the operations will be performed. This positional identification system (10) may be based on different positions of the selection controller (4c) with reference in identification signs (10a) (10b) (10c) (10d) such as colors, alphanumerical signs, drawings, projecting and recessing reliefs, mixed signs, etc. In general, the identification (10) will allow associating each position of the selection controller (4c) with a chamber (2), although it may allow associating the size of the application limb with the chamber (2).

The identifiers (10a)(10b)(10c)(10d) may be arranged on the selector device walls (4), in the outlet connection (5) and inlet connection (8), close to them, in the different tubes, in the armlet walls (1), etc.

Thus, for instance, in a basic system, the identifiers (10) may be arranged on a wall of the selector device (4) with reference to each position of the selection controller (4c).

In a more complex system, the identifiers (10) may also be arranged in a longitudinal edge of the armlet (1) so that, upon wrapping it around the limb, the applied end indicates an identifier (10) which corresponds to another identifier (10) corresponding to the selection controller (4c). it has also been considered the inclusion of identifiers (10) in a transverse edge of the armlet (1), so that, the application length or the perimeter of the limb determines an identifier (10) which is the corresponding to another identifier (10) corresponding to the selection controller (4c), in relation to the width of the chamber and the perimeter of the limb.

For the purpose of facilitating the suitable fixing around limbs of different sizes, it has been considered the inclusion of tightening means (1b)—for example, areas with Velcro—that substantially cover different areas of the armlet (1) and that allow to tighten it totally or partially in any case.

Operation

Upon surrounding with the armlet (1), the end at which it is desirable to measure the blood pressure, the end applied to the armlet (1) matches with any of the identifiers (10) situated on its longitudinal edge. In case of having identifiers (10) on the transverse edges, the forearm extends as far as one of the identifiers (10) [in this case, the identifiers (10) allow observing and deciding at what height of the arm and before the elbow joint, or at what height of the limb on which the pressure is going to be measured, the lower edge of the selected chamber will be placed according to international standards for blood pressure measurement]. In both cases, the selector device (4) allows selecting the positional identifier (10) corresponding to the inflatable chamber(s) (2) that will be enabled.

Figure 3:
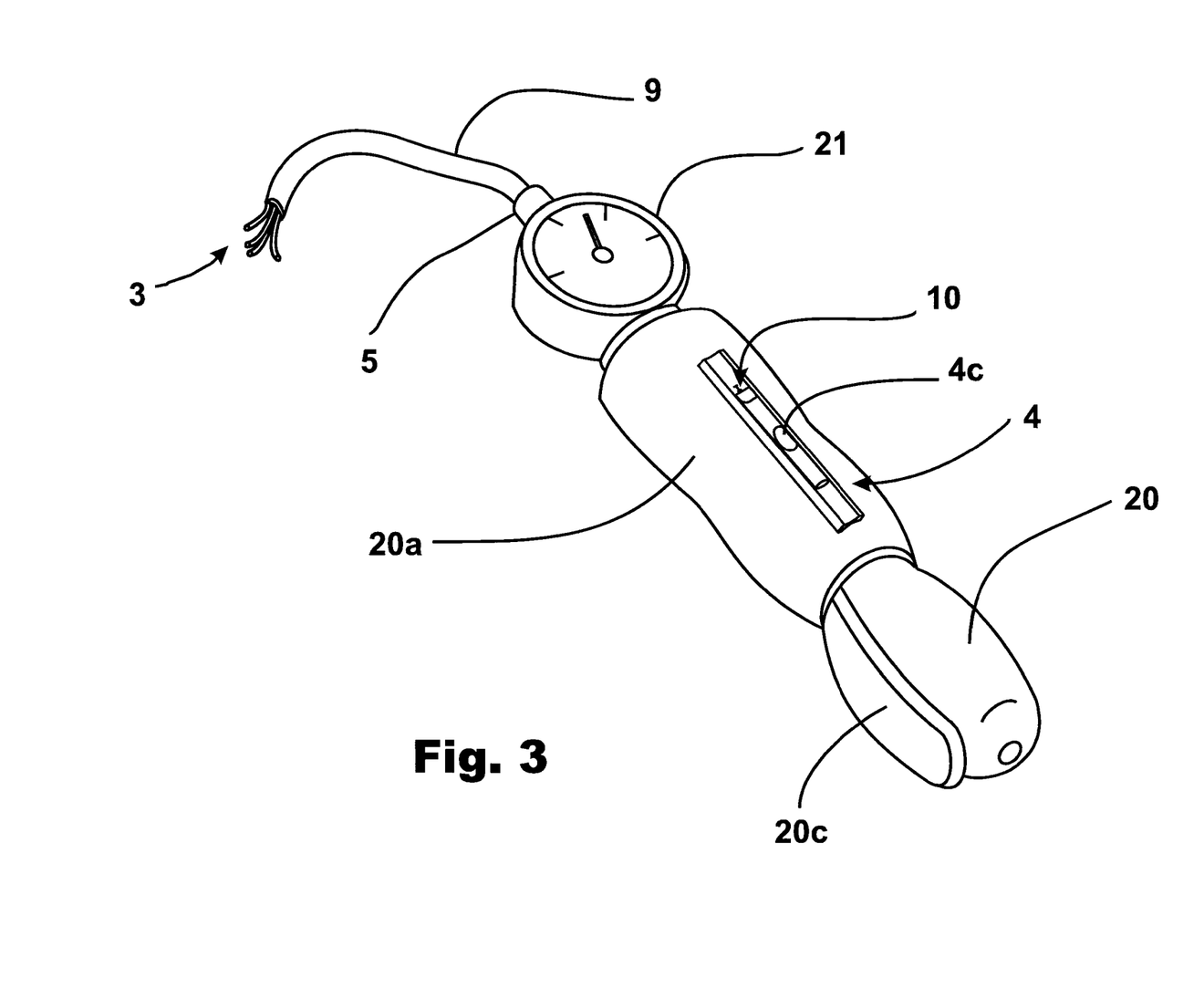
FIG. 3 is a perspective view of the present sphygmomanometer in an embodiment wherein the selector has been incorporated to the operative body or support.

For example, in the cases shown in FIGS. 2 and 3, supposing the positional identification system (10) situated on some of the edges of the armlet (1) determines that the corresponding positional identifier is the second positional identifier (10b), the selection controller (4c) should be displaced as far as the second position (10b) marked in the valve selector device (4).

In these conditions, the outer pneumatic tube (9) and the air press pump (20) are connected to the second inflatable chamber (2b), through the inlet path (7), the second pneumatic outlet path (5b) and the second inner individual pneumatic tube (3b).

In case of FIG. 1, according the corresponding positional identifier (10), it puts the inlet pneumatic connection (8) in the corresponding outlet selective connection (6).

In the case of FIG. 8, the displacement of the valve shutter (4b) allows selective and alternative enabling of one of the pneumatic outlet path (6). Instead, in the cases of FIG. 13, the displacement of the valve shutter (4b) allows selective enabling but integrating and disintegrating pneumatic outlet paths (6) and, therefore, adding or subtracting inflatable chambers (2).

Undoubtedly, upon putting the present invention into practice, modifications may be introduced as far as certain details of construction and form are concerned, without this implying to set apart from the fundamental principles which are clearly explained in the following claims:

The invention claimed is:

1. A multichamber sphygmomanometer having a chamber selector intended to measure blood pressure, which comprises:

an armlet structurally arranged to surround a limb through which there is blood circulation;

a set of inflatable chamber arranged into the armlet, wherein each inflatable chamber has a respective pneumatic connection assigned thereto;

an air pressure pump that, provided with a releasing valve means, is able to inflate the inflatable chamber until reaching the necessary compression on the application limb;

a manometer able to measure the detected blood pressure, an outer pneumatic tube having a first end coupled to the air pressure pump and the manometer and a second end opposite the first end, the outer pneumatic tube connecting the set of inflatable chambers with the air pressure pump and the manometer, the outer pneumatic tube having a plug connection at the second end, the plug connection being configured as a plug that can be plugged into an opening; and a fixed manual valve selector device connected between the outer pneumatic tube and the set of inflatable chambers arranged in the armlet, wherein the assigned pneumatic connections of the inflatable chambers communicate with the outer pneumatic tube, through the fixed manual valve selector device, the fixed manual valve selector device comprising:

at least two outlet selective connections each having an opening into which the plug connection is insertable, wherein each of the at least two outlet selective connections is configured to receive air outputted by the outer pneumatic tube when the air pressure pump is pumped, wherein each of the at least two outlet selective connections is connected to one or more inflatable chambers of the set of inflatable chambers through the fixed manual valve selector device, wherein plugging the plug connection into different ones of the openings of the outlet selective connections connects the air pressure pump to different inflatable chambers through the fixed manual valve selector device, wherein the plug connection is pluggable into one of the openings of the at least two outlet selective connections to establish a connection to one or more inflatable chambers through the fixed manual valve selector device, and the plug connection is separable from the outlet selection connections such that the plug connection can be unplugged from the opening of the one of the at least two output selective connections and then plugged into an opening of another of the at least two output selective connections to establish a connection to a different one or more inflatable chambers, wherein the outlet selective connections have identifiers that associate the different outlet selective connections with the one or more inflatable chambers to which they are connected.

2. The multichamber sphygmomanometer having a chamber selector in accordance with claim 1, which comprises assigned connections and/or selective connections of box and pin type.

3. The multichamber sphygmomanometer having a chamber selector in accordance with claim 1, wherein the fixed manual valve selector device comprises a structure on which a set of tubes is arranged ending at each opposite ends of assigned connection and selective connection.

4. The multichamber sphygmomanometer having a chamber selector in accordance with claim 1, wherein the identifiers include signs and/or colors.

5. The multichamber sphygmomanometer having a chamber selector in accordance with claim 1, wherein the identifiers include identifiers provided on the fixed manual valve selector device and identifiers provided on the armlet, so that the positional identification system identifies which connection or position corresponds to each chamber or set of chambers.

6. The multichamber sphygmomanometer having a chamber selector in accordance with claim 1, wherein the fixed manual valve selector device at least partially mounted into the armlet.

7. The multichamber sphygmomanometer having a chamber selector in accordance with claim 1, wherein the fixed manual valve selector device is arranged outside the armlet.

* * * * *